United States Patent
Guenther et al.

(10) Patent No.: US 12,384,639 B2
(45) Date of Patent: Aug. 12, 2025

(54) ROLL-UP DEVICE AND WRAPPING SYSTEM

(71) Applicants: Catrina Guenther, White Lake, MI (US); John P. Guenther, White Lake, MI (US)

(72) Inventors: Catrina Guenther, White Lake, MI (US); John P. Guenther, White Lake, MI (US)

(*) Notice: Subject to any disclaimer, the term of this patent is extended or adjusted under 35 U.S.C. 154(b) by 101 days.

(21) Appl. No.: 18/038,087

(22) PCT Filed: Nov. 22, 2021

(86) PCT No.: PCT/US2021/060274
§ 371 (c)(1),
(2) Date: May 22, 2023

(87) PCT Pub. No.: WO2022/109372
PCT Pub. Date: May 27, 2022

(65) Prior Publication Data
US 2023/0365367 A1    Nov. 16, 2023

Related U.S. Application Data

(60) Provisional application No. 63/129,180, filed on Dec. 22, 2020, provisional application No. 63/117,199, filed on Nov. 23, 2020.

(51) Int. Cl.
*B65H 18/10* (2006.01)
*A61F 15/00* (2006.01)
*B65H 75/28* (2006.01)

(52) U.S. Cl.
CPC ........... *B65H 18/10* (2013.01); *A61F 15/007* (2013.01); *B65H 75/28* (2013.01);
(Continued)

(58) Field of Classification Search
CPC ..................................... A61F 15/007
See application file for complete search history.

(56) References Cited

U.S. PATENT DOCUMENTS 409,447 A * 8/1889 Block ............... B65H 18/10
                                            242/548.2
437,554 A * 9/1890 Bellamy ............ B65H 54/585
                                            242/532.6
(Continued)

FOREIGN PATENT DOCUMENTS

CH          536 110      * 10/1972
CN      109808937 A       5/2019
(Continued)

OTHER PUBLICATIONS

International Preliminary Report on Patentability dated May 16, 2023, PCT/US2021/60274.

*Primary Examiner* — William A. Rivera

(57) ABSTRACT

A wrapping or roll-up device including a base, one or more connectors, an arm, and a handle. In embodiments, one or more connectors are connected to the base and are configured to connect the device to a wall or support structure, and/or the arm includes an aperture. In embodiments, a handle includes an extended portion and a grip portion, and at least a portion of the extended portion is configured to extend through the aperture. Further, with embodiments, the extended portion includes a slot disposed about an end of the extended portion. Embodiments may include a tensioner. Methods for wrapping or rolling up an article such as a wrap are also disclosed.

25 Claims, 20 Drawing Sheets

(52) U.S. Cl.
CPC .............. *B65H 2301/41306* (2013.01); *B65H 2301/41446* (2013.01); *B65H 2301/5115* (2013.01); *B65H 2402/43* (2013.01); *B65H 2403/941* (2013.01); *B65H 2404/69* (2013.01)

(56) References Cited

U.S. PATENT DOCUMENTS

| | | | | |
|---|---|---|---|---|
| 506,913 | A | * | 10/1893 | Jobse ................ B65H 18/08 242/615 |
| 683,774 | A | * | 10/1901 | Kilbourn ............ B65H 18/08 242/615 |
| 3,647,152 | A | * | 3/1972 | Trewella ............ A61F 15/007 242/532.5 |
| 3,998,402 | A | * | 12/1976 | Christensen ........ B65H 18/10 242/399 |
| 4,892,265 | A | | 1/1990 | Cox |
| 5,265,818 | A | | 11/1993 | Nakasone |
| D390,094 | S | * | 2/1998 | Pamplin ................ D12/400 |
| 5,961,061 | A | * | 10/1999 | Stanley ............. B65H 54/585 242/395 |
| 6,439,502 | B1 | | 8/2002 | Gemmell et al. |
| 7,766,271 | B1 | * | 8/2010 | Confoey ............. B60P 7/0846 242/395 |
| 9,004,391 | B2 | * | 4/2015 | Fernandez ......... B65H 75/4492 242/588.2 |
| 2004/0108404 | A1 | * | 6/2004 | Wiermaa ............ B65H 18/10 242/532.6 |
| 2005/0092862 | A1 | * | 5/2005 | Treat ................. B60P 7/0846 242/395 |
| 2008/0029287 | A1 | | 2/2008 | Korcz et al. |
| 2012/0193465 | A1 | * | 8/2012 | Fernandez ......... B65H 75/4492 242/539 |
| 2018/0014701 | A1 | | 1/2018 | Kennedy |
| 2019/0331288 | A1 | | 10/2019 | Gupta |

FOREIGN PATENT DOCUMENTS

| | | | |
|---|---|---|---|
| DE | 20215339 U1 | | 12/2002 |
| GB | 110136 | * | 10/1917 |
| WO | 2016036859 A | | 3/2016 |
| WO | WO 2023/126794 | * | 7/2023 |

* cited by examiner

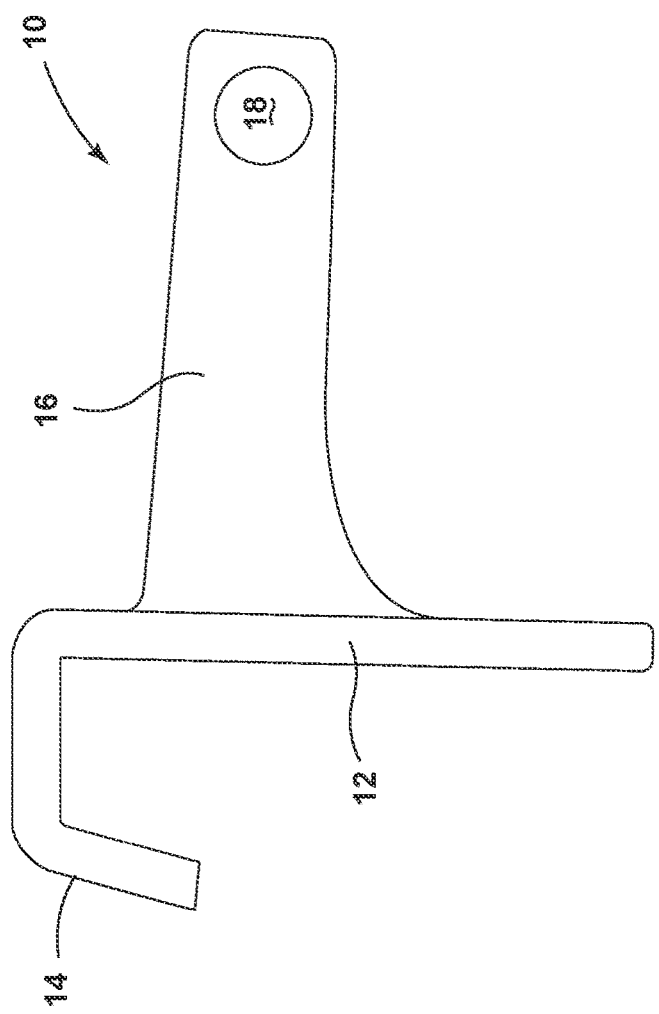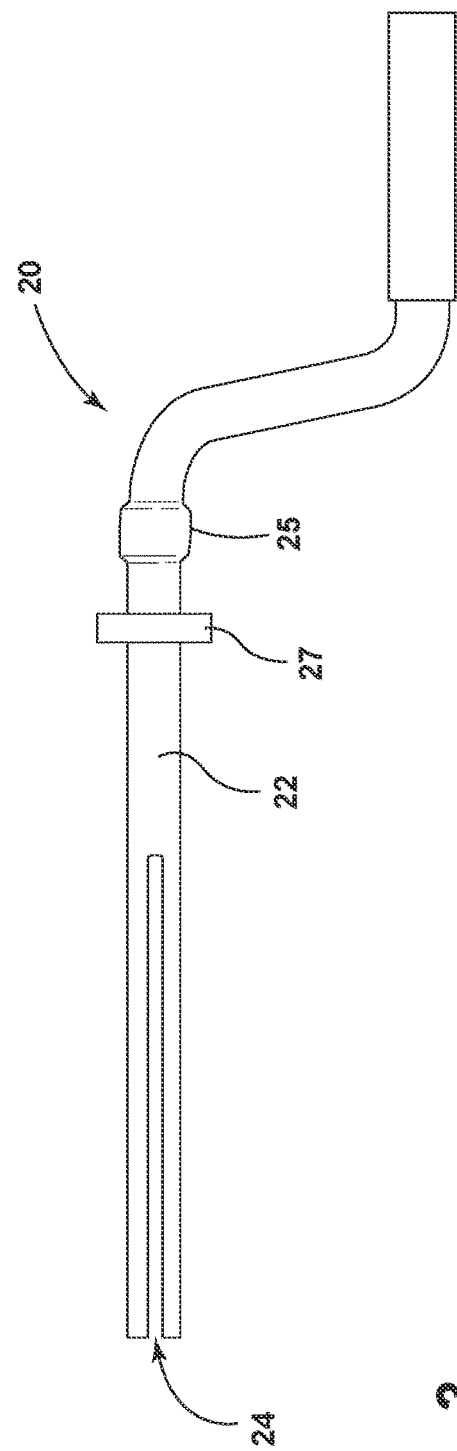
FIG. 2
FIG. 3

ROLL-UP DEVICE AND WRAPPING SYSTEM

CROSS-REFERENCE TO RELATED APPLICATIONS

This application is a National Stage Patent Application of International Patent Application No. PCT/US21/60274, filed Nov. 21, 2021, which claims the benefit of priority to U.S. Provisional Patent Application No. 63/129,180, filed Dec. 22, 2020 and U.S. Provisional Patent Application No. 63/117,199, filed Nov. 23, 2020, the contents of all of the foregoing being incorporated by reference in their entireties.

TECHNICAL FIELD

The present disclosure generally relates to roll-up devices and wrapping systems, including devices and systems for rolling up or re-wrapping straps.

BACKGROUND

This background description is set forth below for the purpose of providing context only. Therefore, any aspect of this background description, to the extent that it does not otherwise qualify as prior art, is neither expressly nor impliedly admitted as prior art against the instant disclosure.

In industries, including medical and equestrian industries, articles or items, such as wraps, may be used or otherwise become unraveled. For example, wraps may be used to wrap a horse's leg for riding. When finished, such wraps may need to be re-wound. However, such rewinding may be messy, as the wraps may pick up hay, dust, or other debris, and time consuming, as the wraps may be lengthy and can take time to fully roll up. Moreover, as horses are moved or exist in a number of locations, it is beneficial to provide a device that can readily be moved or repositioned for use or storage.

For at least these reasons, there is a desire for a wrapping or roll-up device that address some or all of the existing challenges and/or provided added benefits.

SUMMARY

A wrapping or roll-up device including a base, one or more connectors, an arm, and a handle. In embodiments, one or more connectors are connected to the base and are configured to connect the device to a wall or support structure, and/or the arm includes an aperture. In embodiments, a handle includes an extended portion and a grip portion, and at least a portion of the extended portion is configured to extend through the aperture. Further, with embodiments, the extended portion includes a slot disposed about an end of the extended portion.

The foregoing and other aspects, features, details, utilities, and/or advantages of embodiments of the present disclosure will be apparent from reading the following description, and from reviewing the accompanying drawings.

BRIEF DESCRIPTION OF THE DRAWINGS

FIG. 2 is a side view of a portion of an embodiment of a wrapping or roll-up device according to aspects or teachings of the present disclosure.

FIG. 3 is a perspective view of a handle for a wrapping or roll-up device according to aspects or teachings of the present disclosure;

DETAILED DESCRIPTION

Reference will now be made in detail to embodiments of the present disclosure, examples of which are described herein and illustrated in the accompanying drawings. While the present disclosure will be described in conjunction with embodiments and/or examples, it will be understood that they do not limit the present disclosure to these embodiments and/or examples. On the contrary, the present disclosure covers alternatives, modifications, and equivalents.

Various embodiments are described herein for various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments.

Figure 1:
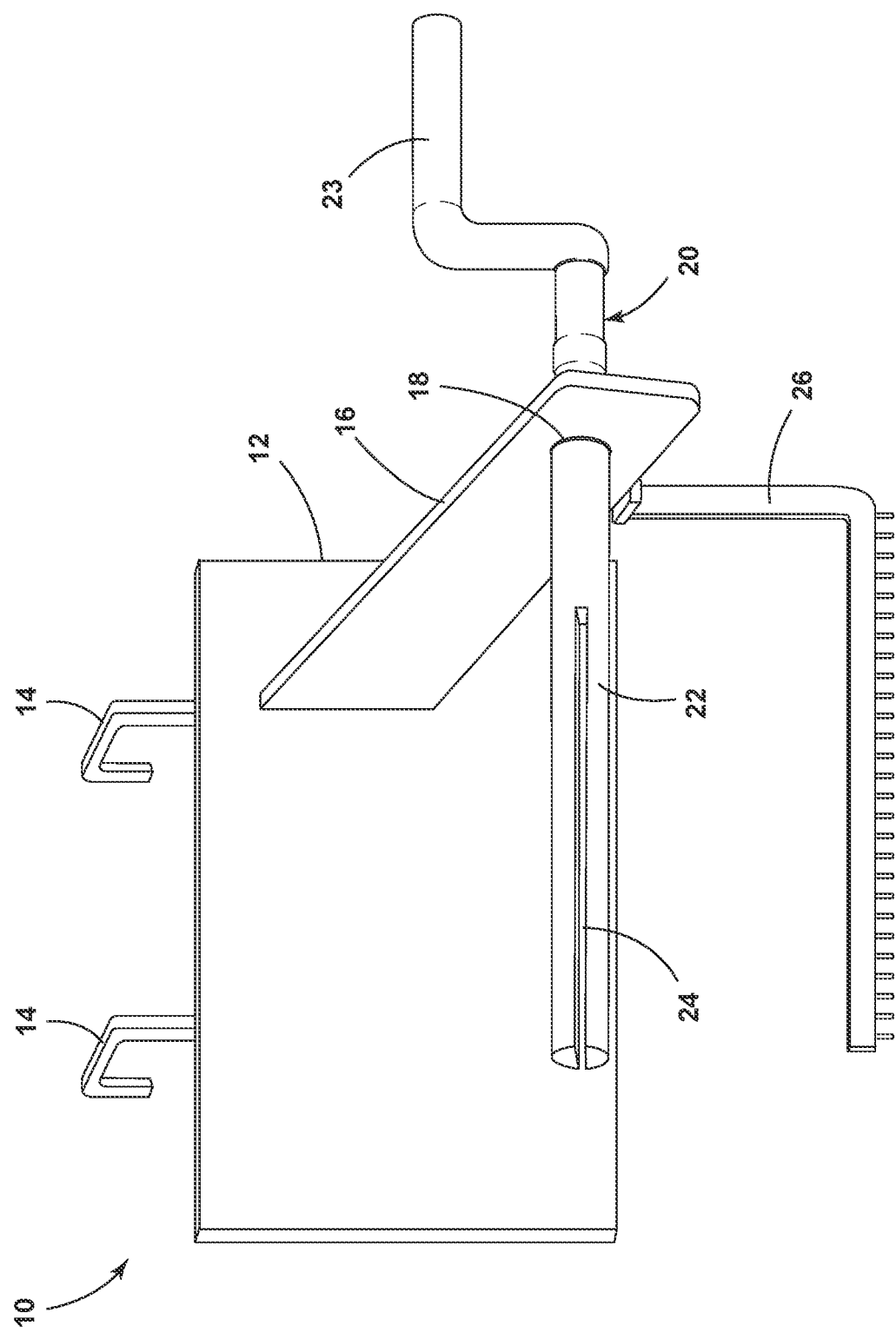
FIG. 1 is a perspective view of an embodiment of a wrapping or roll-up device according to aspects or teachings of the present disclosure.

Referring now to FIG. 1, an embodiment of a wrapping (or roll-up) device 10 according to aspects or teachings of the present disclosure. As generally illustrated, a wrapping device 10 may include a base 12, one or more connectors (e.g., one or more hooks 14), an arm 16, an opening or aperture 18, and a handle 20. In embodiments, such as generally illustrated, a handle 20 may include an extended portion 22, a grip portion 23, and a slot 24.

As generally shown in FIG. 1, the device 10 may include one or more connectors (e.g., hooks 14) that may be connected to and/or extend from a base 12 to permit the device 10 to be connected or attached to a wall and/or other support structure. The connectors (e.g., hook(s) 14) may be connected to the base 12 or, for some embodiments, may be formed as an integral or unitary portion of a base 12. For example and without limitation, an embodiment of a device 10 may include one or more hooks (or hook-like features) 14 that can extend from a base 12 and connect or attach to (e.g., hang on) a portion of a wall or other support structure. The one or more connectors (such as hooks 14) can be configured so that the device 10 may be portable and, as such, may be connected and disconnected at various positions and/or locations. For instance, with some applications, a device 10 may be connected to a portion of a stall, a wall, or other structure in a barn.

In embodiments, an extended portion 22 of a handle 20 may extend through an aperture 18 provided in arm 16. As generally illustrated, such an extended portion 22 may include a slot 24 that extends from an and of the extended portion 22 that is more remote from the arm 16, and the slot 24 may be configured to receive or retain a portion of an article (e.g., a wrap or bandage) that is to be rolled up or wrapped.

Additionally, with some embodiments, the device 10 may include a cleaner or brush 26. In embodiments, a cleaner or brush 26 may be formed integrally with or connected to a portion of a device 10, such as a base 12 or an arm 16. The cleaner or brush 26 may be configured to include one or more bristles or scrapers that may dislodge and/or remove debris or other undesired materials from an article as portions of the article contact or brush by the cleaner or brush 26. In embodiments, a cleaner or brush 26 may be rigid or may be biased in a position and may move slightly (e.g., rotate about a connection pivot) as an article, or portion thereof, moves upwardly as it is wrapped or rolled up.

FIG. 2 generally illustrates a side view of a portion of an embodiment of a wrapping or roll-up device 10 according to aspects or teachings of the present disclosure. In embodiments, one or more connectors 14 may be formed integrally with a base 12. The arm 16 may include an aperture 18 that is configured (e.g., sized, shaped, etc.) to receive and support a portion of a handle 20. An embodiment of a handle 20 is generally illustrated in FIG. 3. As generally illustrated, a handle 20 may include a slot 24 and/or a formation (e.g., radially extending formation 25 that may be configured as a bump or ridge). The radially extending formation 25 may be formed separately or integrally with the extended portion 22 of the handle 20, and the radially extending formation 25 may be sized to connect with a portion of the extended portion and may be configured to prohibit the movement of the extended portion 22 through the aperture 18. In embodiments, a separate connecting/locking component 27 may be included, and may be configured to retain or impede the extended portion 22 within the aperture 18 of the arm 16 and/or from movement in relation to the aperture 18 (e.g., translation through or in/out of the aperture).

Figure 5:
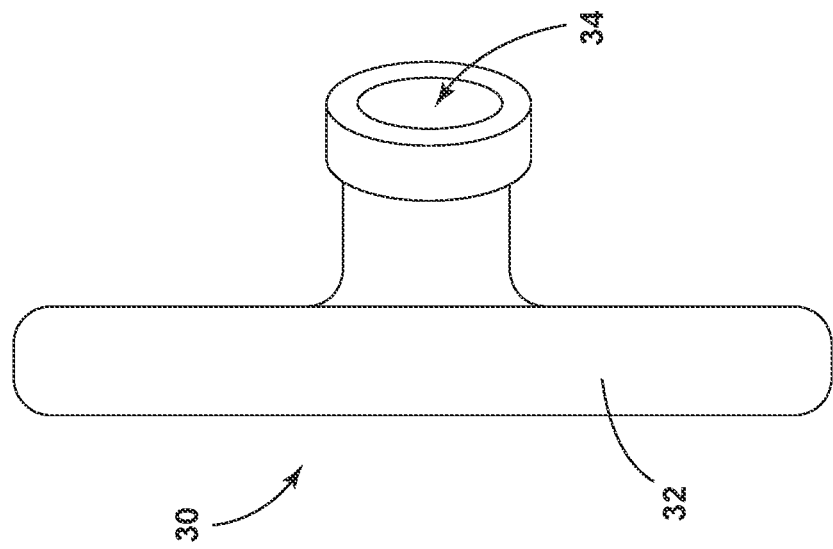
FIG. 5 is a perspective view of another embodiment of a holder for a wrapping or roll-up device according to aspects or teachings of the present disclosure.
Figure 4:
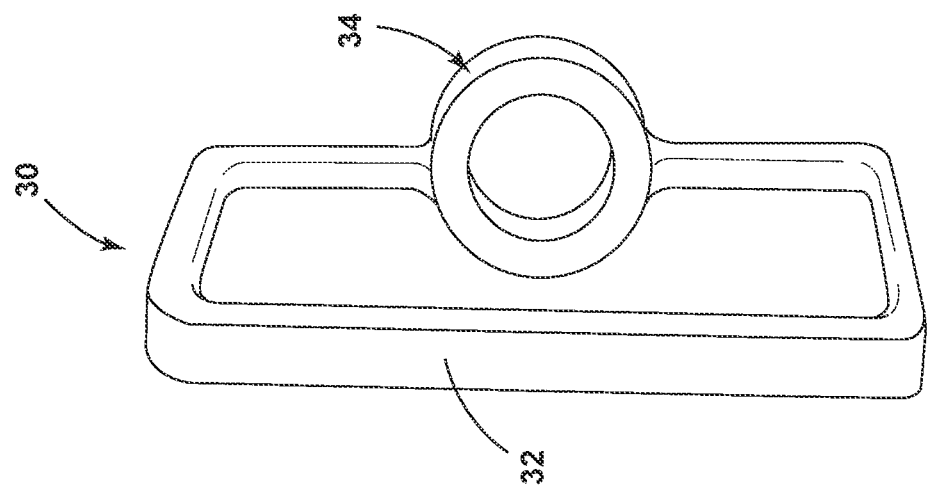
FIG. 4 is a perspective view of an embodiment of a holder for a wrapping or roll-up device according to aspects or teachings of the present disclosure.

FIG. 4 generally illustrates an embodiment of a holder 30 that may be used in connection with a wrapping or roll-up device 10. A holder 30 may include a grip portion 32 and a receiving portion 34. A grip portion 32 may include a portion that is configured to be grasped and/or held by a user. A receiving portion 34 may be configured to receive a portion of an extended portion 22 of a handle 20. In embodiments, a receiving portion may be configured to receive a portion of a handle 20 and to permit a portion (e.g., extended portion 22) to rotate with the rotation of a handle. Another embodiment of a holder 30 is generally illustrated in FIG. 5. However, the disclosure is not limited to the illustrated holders, and other forms of holders may be used in connection with the present concept.

Figure 6:
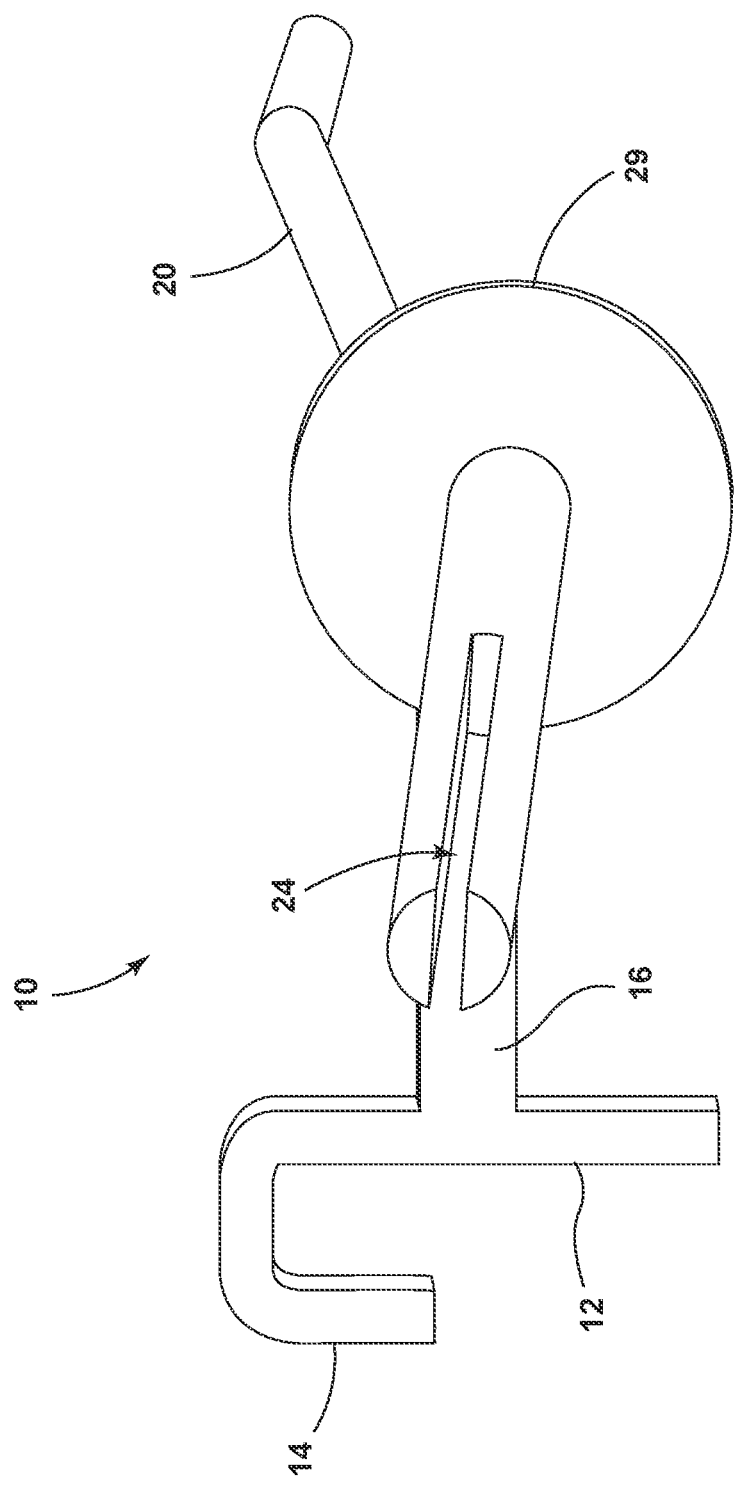
FIG. 6 is a perspective view of another embodiment of a wrapping or roll-up device according to aspects or teachings of the present disclosure.

FIG. 6 generally illustrates another embodiment of a wrapping or roll-up device 10 in according to aspects or teachings of the present disclosure. As generally illustrated, the device 10 may include at least one connector 14 and may include a plate 29 that is disposed on a side of an aperture in an arm 16. As generally illustrated, a connector, a base 12, and/or an arm 16 may be formed integrally as a single unitary formation. In embodiments, a plate 29 (or other guide or boundary-type formation) may, inter alia, be configured to serve as a guide or boundary for an article (e.g., a strap or horse wrap) that is being rolled up or wrapped.

Figure 7:
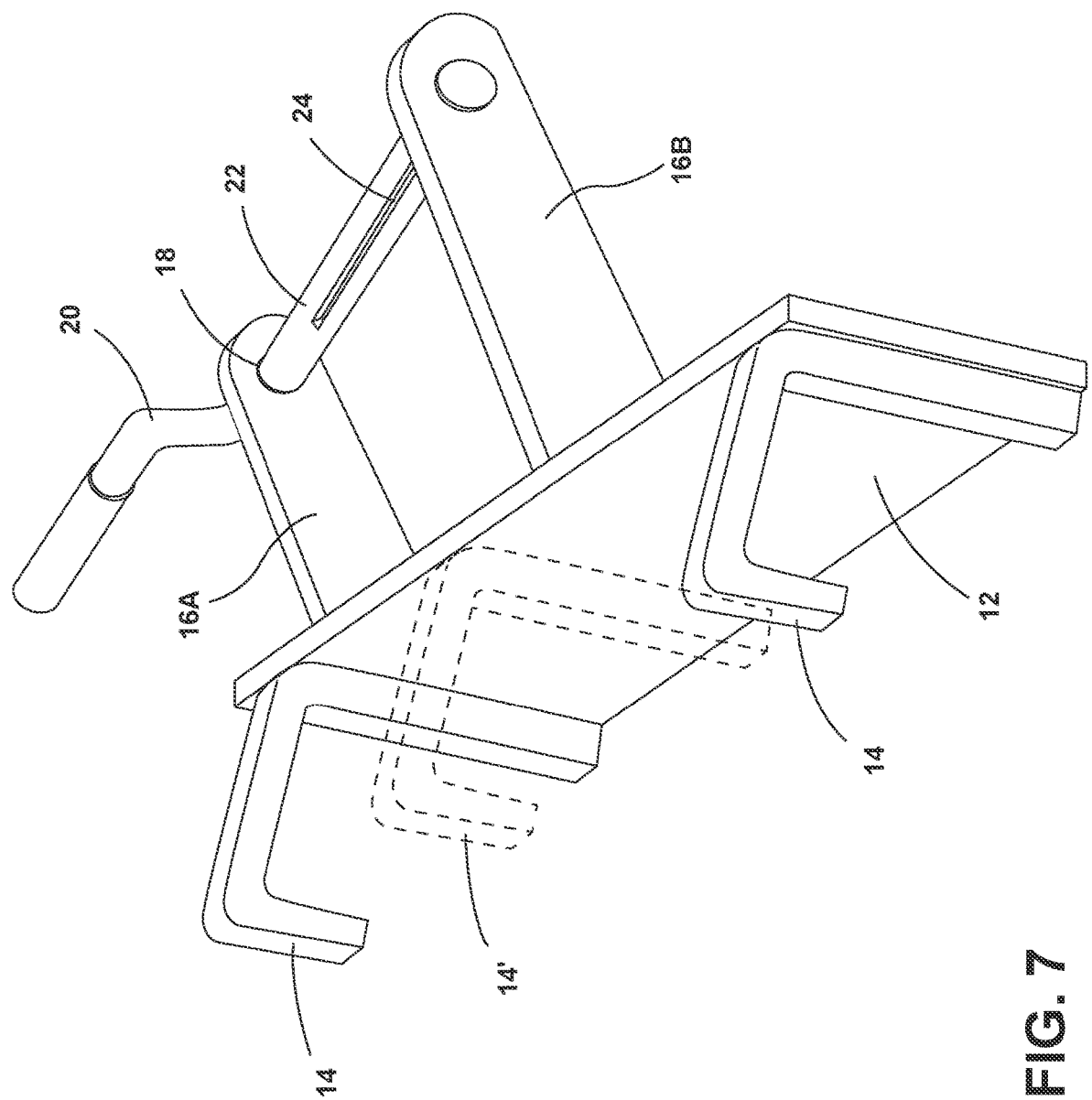
FIG. 7 is a perspective view of yet another embodiment of a wrapping or roll-up device according to aspects or teachings of the present disclosure.

Turning to FIG. 7, another embodiment of a wrapping or roll-up device 10 is generally illustrated. The device 10 may include one or more connectors 14 that may be configured for attachment to a wall or support structure. As generally shown, embodiments of such a device may include two arms (e.g., 16A, 16B), which may be disposed at or about different/opposite ends of an extended portion 22 of a handle 20.

Figure 8:
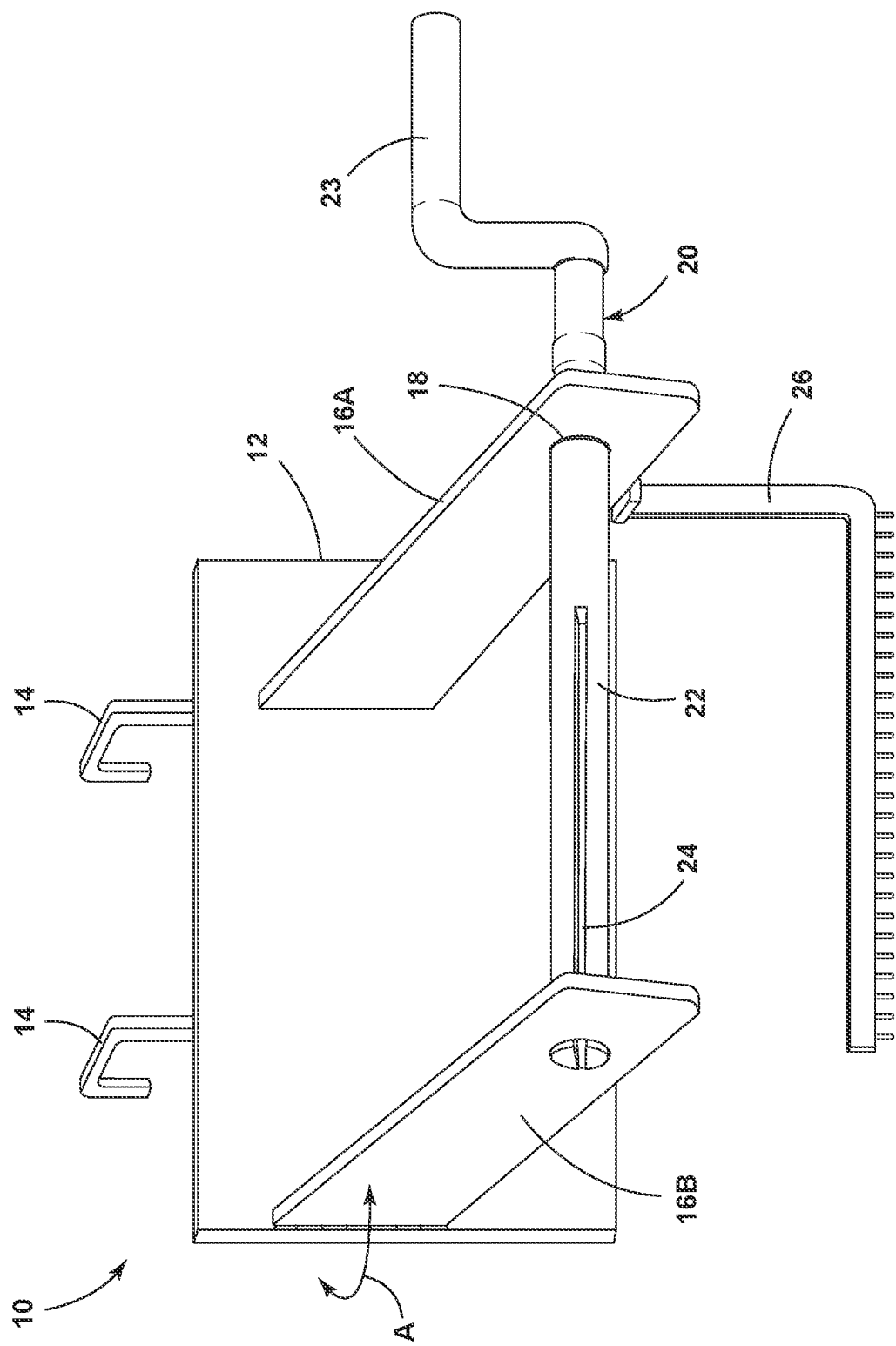
FIG. 8 is a perspective view of still another embodiment of a wrapping or roll-up device according to aspects or teachings of the present disclosure.
Figure 9:
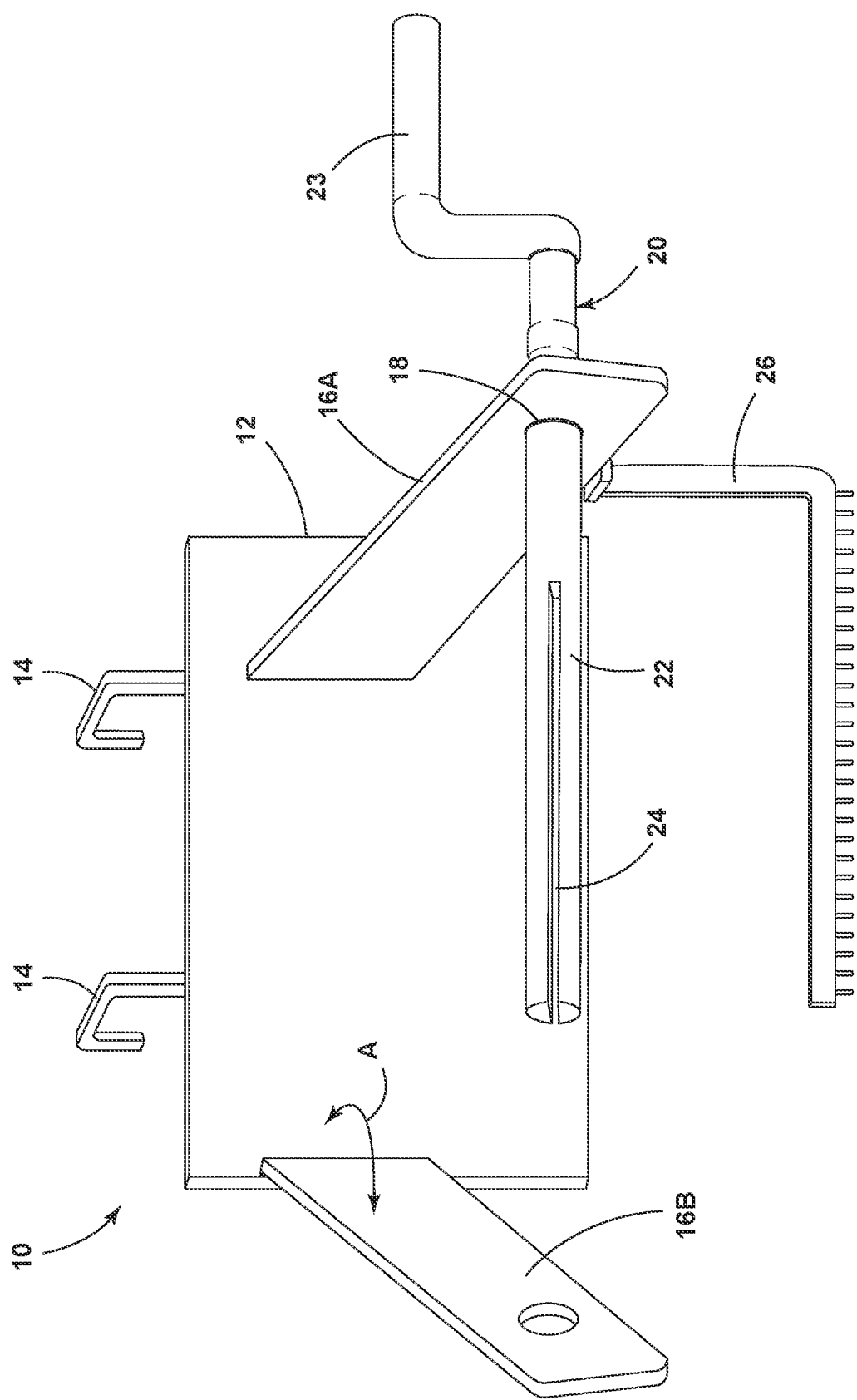
FIG. 9 is a perspective view of an embodiment of a wrapping or roll-up device, similar to that shown in FIG. 8, and shown in an open position/configuration.

Another embodiment of a wrapping or roll-up device having two arms (e.g., 16A, 16B) is generally illustrated in FIG. 8. As generally illustrated, a first arm 16A may include an aperture 18 for receiving a portion of a handle 20 therethrough. In embodiments, first arm 16A may be rigidly connected to a base 12, and there may be little positional movement between the base 12 and the first arm 16A. With embodiments, such as generally illustrated, second arm 16B may be configured to receive a portion of an extended portion 22 of handle 20, such as in a recess or aperture in second arm 16B. Further, as generally illustrated (via arrow A), second arm 16B may be configured to move/rotate/pivot away from an extended portion of a handle, for example, to permit a loading and/or unloading of an article to be rolled or wrapped up. For example and without limitation, arm 16B may be hinged to swing apart from handle 20. Such hinged connection may be in the form of an integral hinge or a hinge formed with additional components connected to base 12. Embodiments of a device 10 may also include a cleaner or brush 26 and/or a tensioning formation. The cleaner or brush 26 may be configured to include one or more bristles or scrapers that may dislodge and/or remove debris or other undesired materials from an article as portions of the article contact or brush by the cleaner or brush 26. In embodiments, a cleaner or brush 26 may be formed with, or connected to, a portion of base 12 and/or arm 16A. FIG. 9 generally illustrates a wrapping or roll-up device 10 that may be similar to that shown in FIG. 8, and is shown with arm 16B in an open position/configuration.

For example and without limitation, with a wrapping or roll-up device 10, an end portion of an article to be rolled up or wrapped may be positioned through a portion of a slot 24—which may extend from an end of an extended portion 22 of a handle. In embodiments, that include a second arm 16B (such as generally illustrated in FIGS. 7-9), a second arm 16B may be first opened (see, e.g., FIG. 9) to permit an end of such an article to be inserted into/through slot 24. Once the article is connected to the handle 20 as such, the handle may be turned (clockwise or counterclockwise) to roll/wrap up the article. In embodiments that include a holder 30, such a holder 30 may be used to help position and/or retain the article on or about the handle as the article is rolled up/wrapped up. In embodiments that include a second arm 16B, such arm 16B may be closed and/or connected to a portion of the handle as the handle is rotated to roll up/wrap up the article. Additionally, with embodiments that include a cleaner or brush 26, the article may be draped over or positioned to brush by the cleaner or brush 26 as portions of the article move by such cleaner or brush 26.

Figure 10:
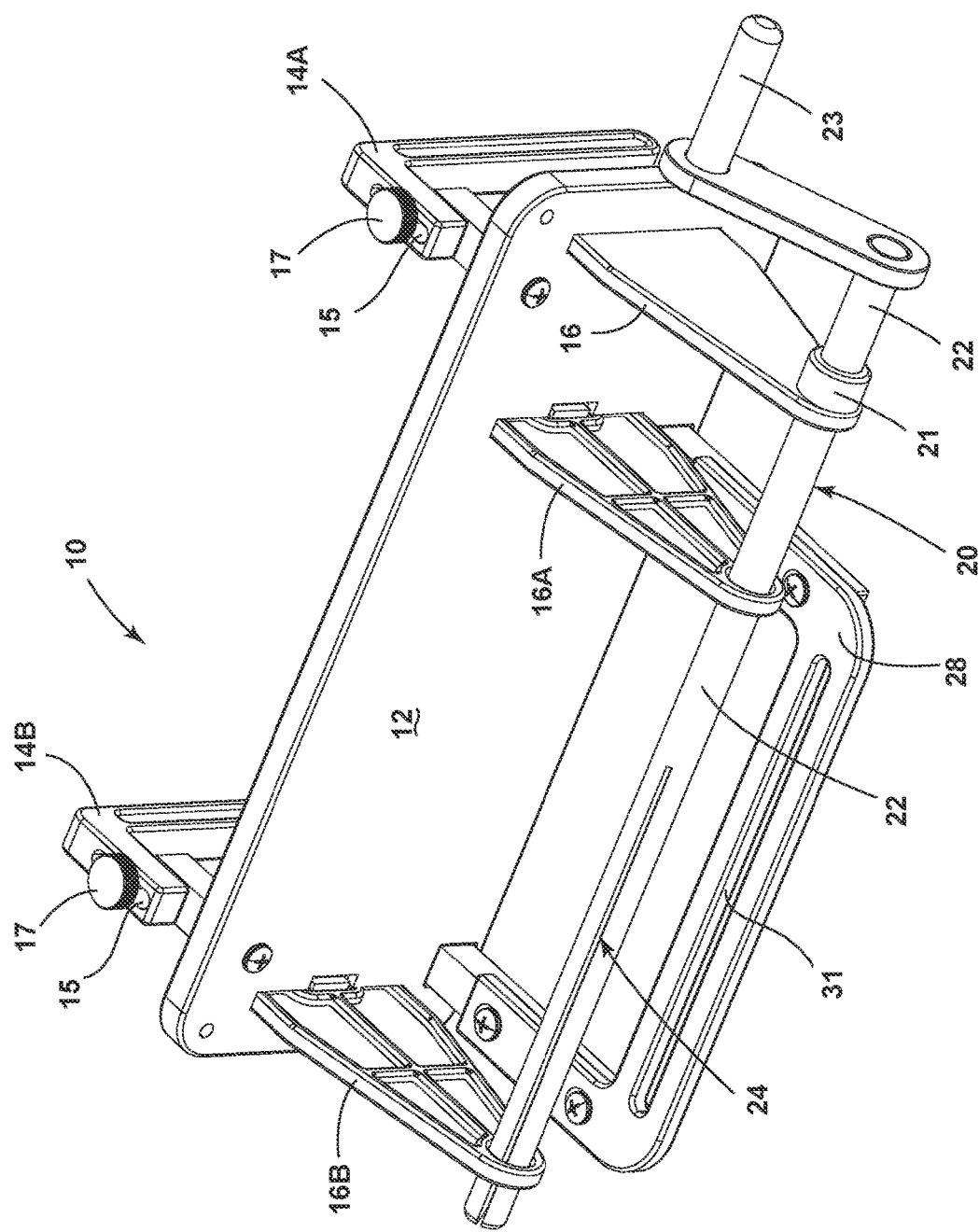
FIG. 10 is a front-top-side perspective view of an embodiment of a wrapping or roll-up device according to aspects or teachings of the present disclosure.
Figure 11:
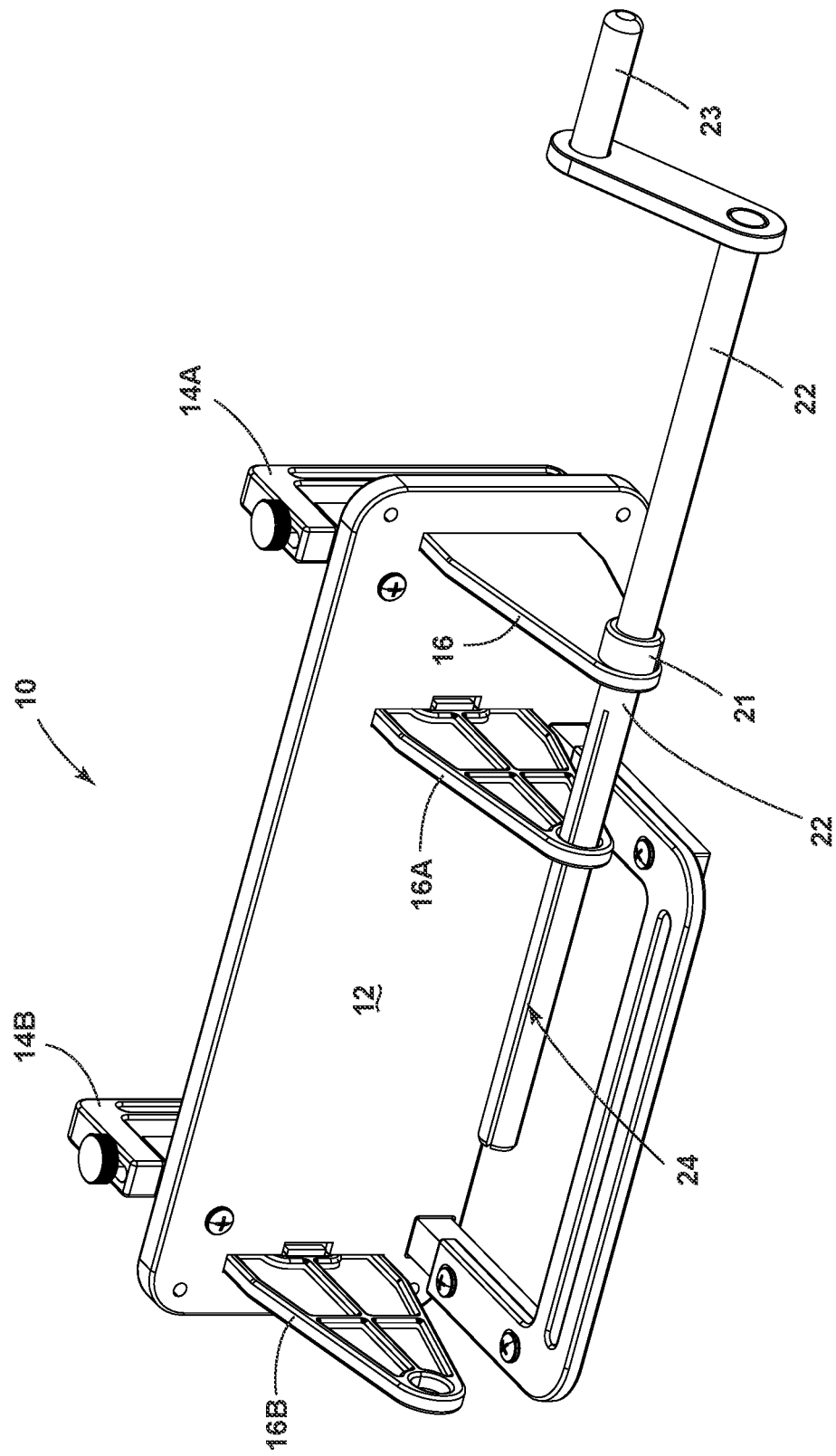
FIG. 11 is a front-top-side perspective view of the embodiment of a wrapping or roll-up device shown in FIG. 10.
Figure 12:
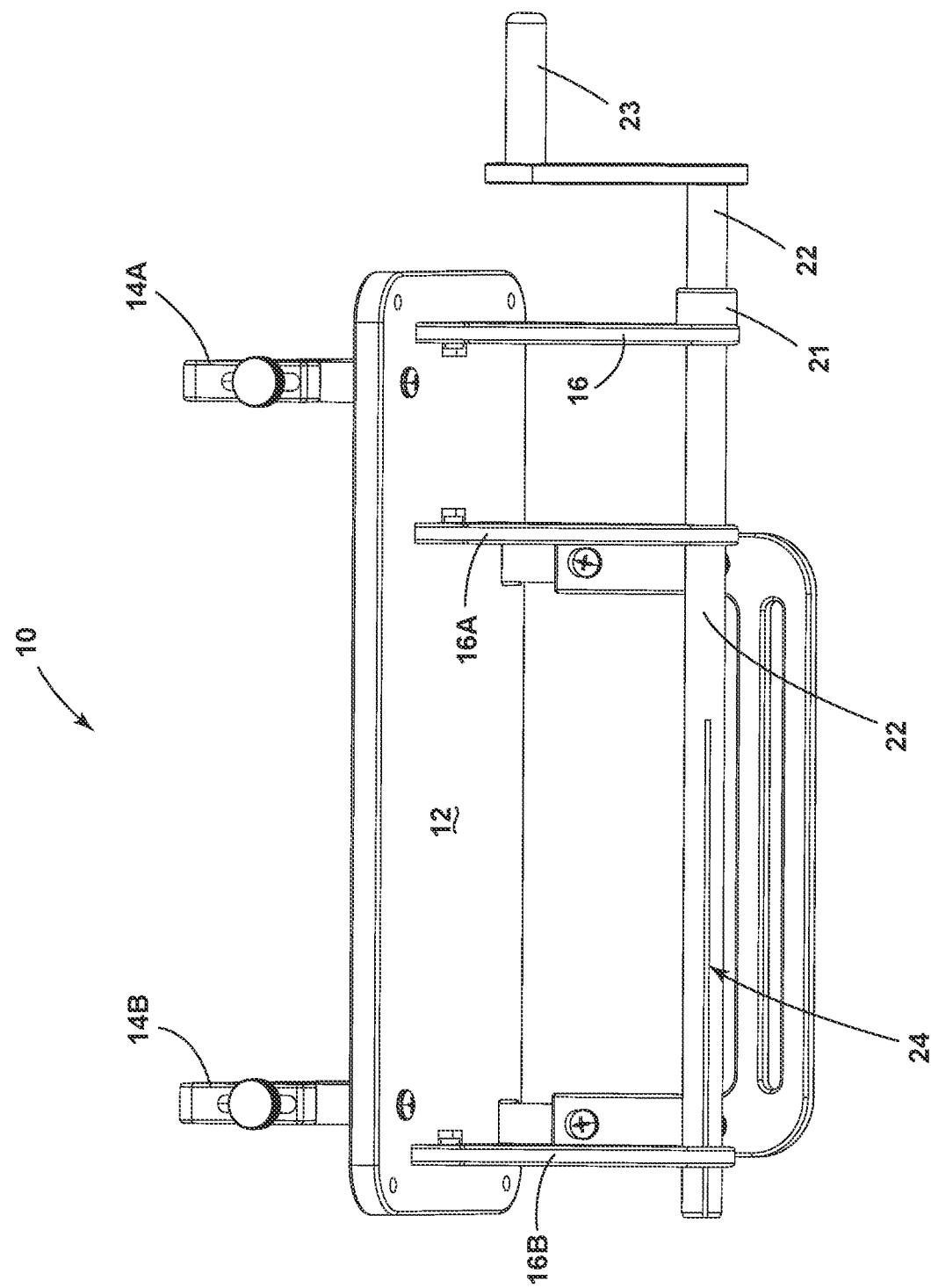
FIG. 12 is a front-top perspective view of the embodiment of a wrapping or roll-up device shown in FIG. 10.
Figure 13:
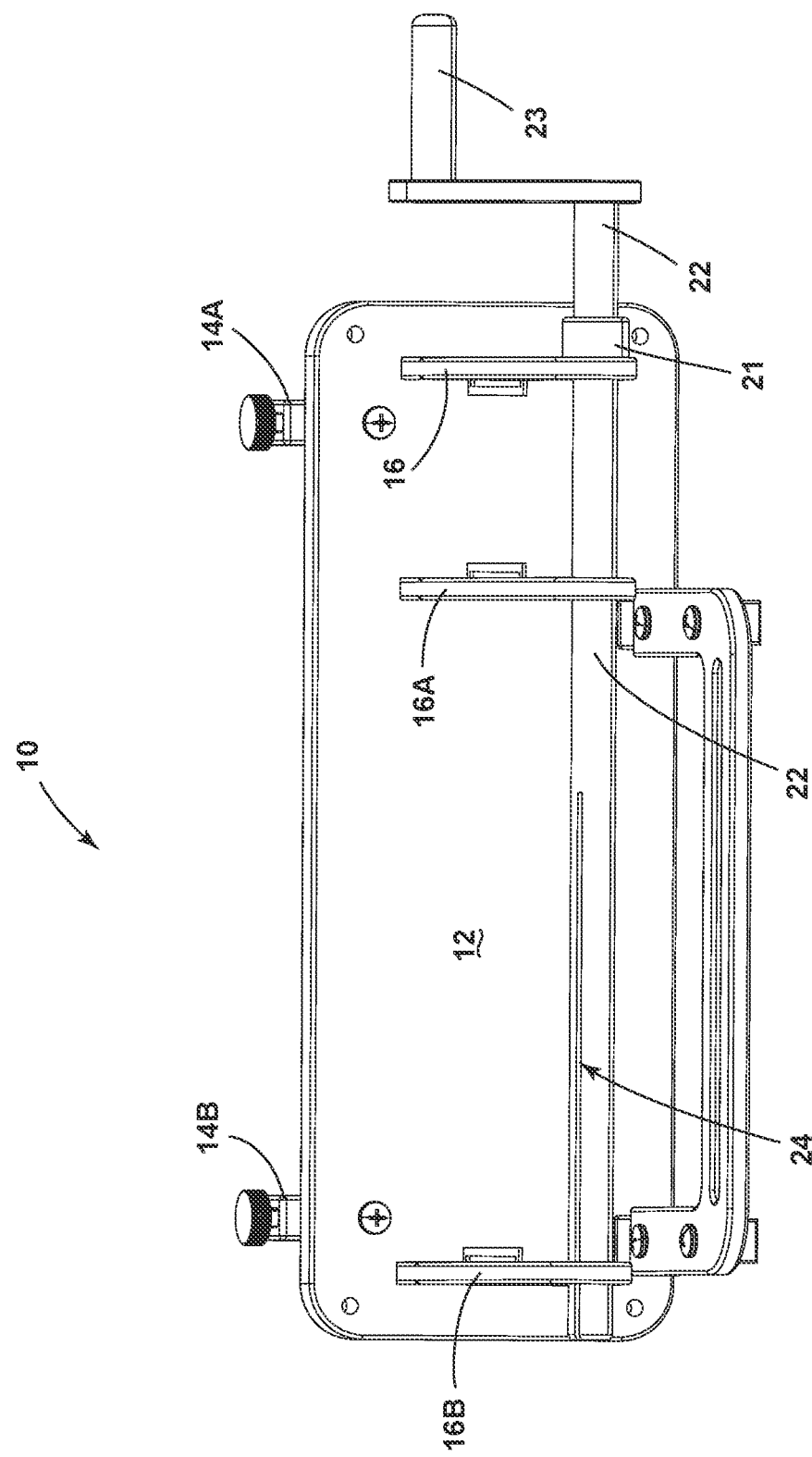
FIG. 13 is a front-top perspective view of the embodiment of a wrapping or roll-up device shown in FIG. 10.

Another embodiment of a wrapping (or roll-up) device 10 according to aspects or teachings of the present disclosure is generally illustrated in FIG. 10. As generally illustrated, the wrapping device 10 may include a base 12, one or more connectors 14 (e.g., 14A, 14B), at least one arm (e.g., 16, 16A) having an aperture or through-hole 18, and a handle 20.

In embodiments, the device 10 may include a tensioner 28. A tensioner 28 may be connected to, and extend from (e.g., perpendicular to) the base 12. The tensioner 28 may be disposed vertically below the handle 20 and may be configured to provide tension (e.g., a slight pulling friction or resistance) to a portion of a wrap or article being rolled up/wrapped up by the device 10—for example, to facilitate a tighter wrapping of a wrap or article. In embodiments, a tensioner 28 may comprise a beam or other horizontally extending structure or formation that provides some resistance to the rolling of the wrap or article. In some embodiments, such as illustrated, the tensioner 28 may include a slot (or slit) 31 or other form of opening that permits a wrap or article to extend therethrough and up to the handle. In embodiments, means or feature for brushing or cleaning a wrap—such as a set of bristles—may be included in connection with a tensioner 28 and/or slot 31.

In the illustrated embodiment, a handle is extended through two arms 16, 16A, which can provide alignment and support. Although, such a second arm 16A may be optional for some embodiments. The arms may be rigidly connected to the base 12—whether integrally formed therewith or attached or connected thereto. By way of example and without limitation, embodiments of connectors 14 may take the form of a hook, form of overhanging formation or feature, or other connectors for connection or attachment to a support surface such as a wall. While portability is commonly advantageous, if desired, a user could permanently or semi-permanently attach a device to a wall or other external formation (for example, by connecting the base 12 to a wall, such as by nail, screw, zip tie, and/or other fasteners). In embodiments, a device may be fastened (e.g., directly fastened), permanently or temporarily, to a support structure (such as a wall). For example and without limitations, a base 12 may include one or more locations and/or apertures that may facilitate the connection (e.g., by nailing or screwing) of a device 10 to a support structure. With such embodiments, a base may not need or include one or more connectors (e.g., a hook to extend over a portion of a wall).

Figure 14:
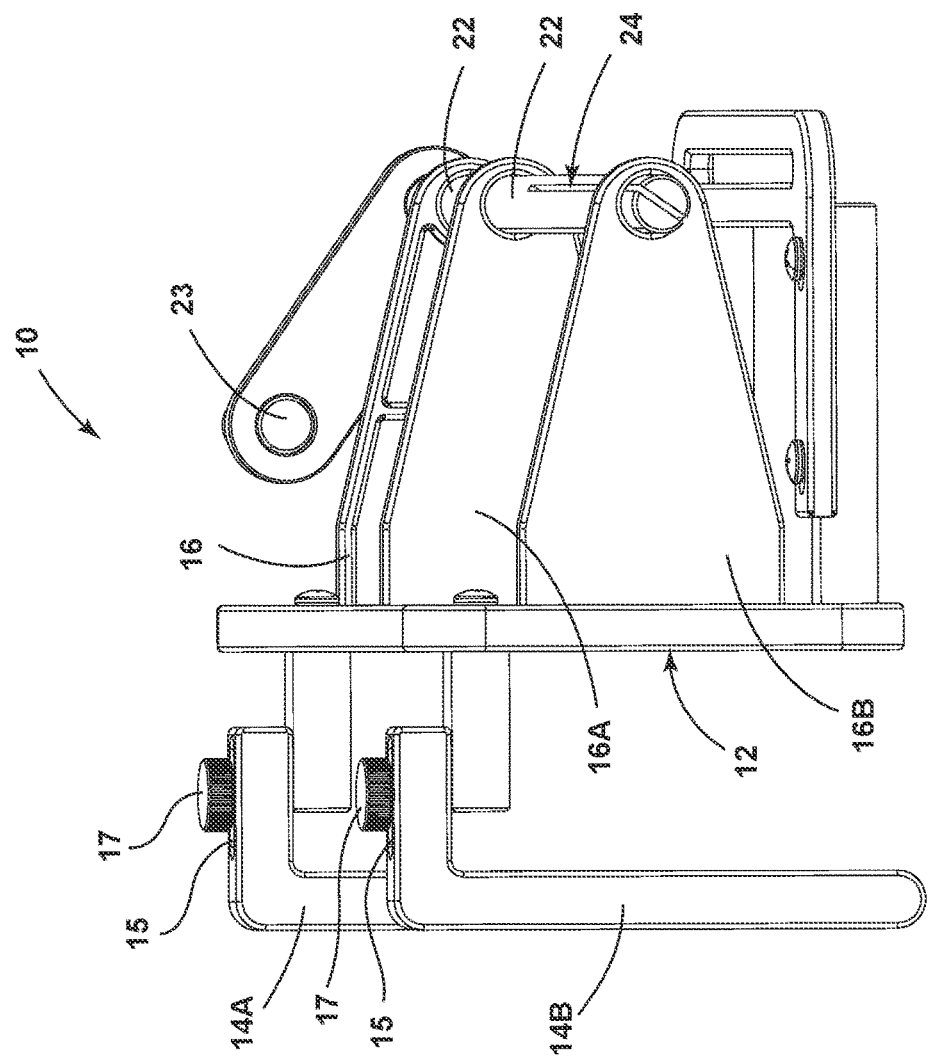
FIG. 14 is a side-top-rear perspective view of the embodiment of a wrapping or roll-up device shown in FIG. 10.
Figure 15:
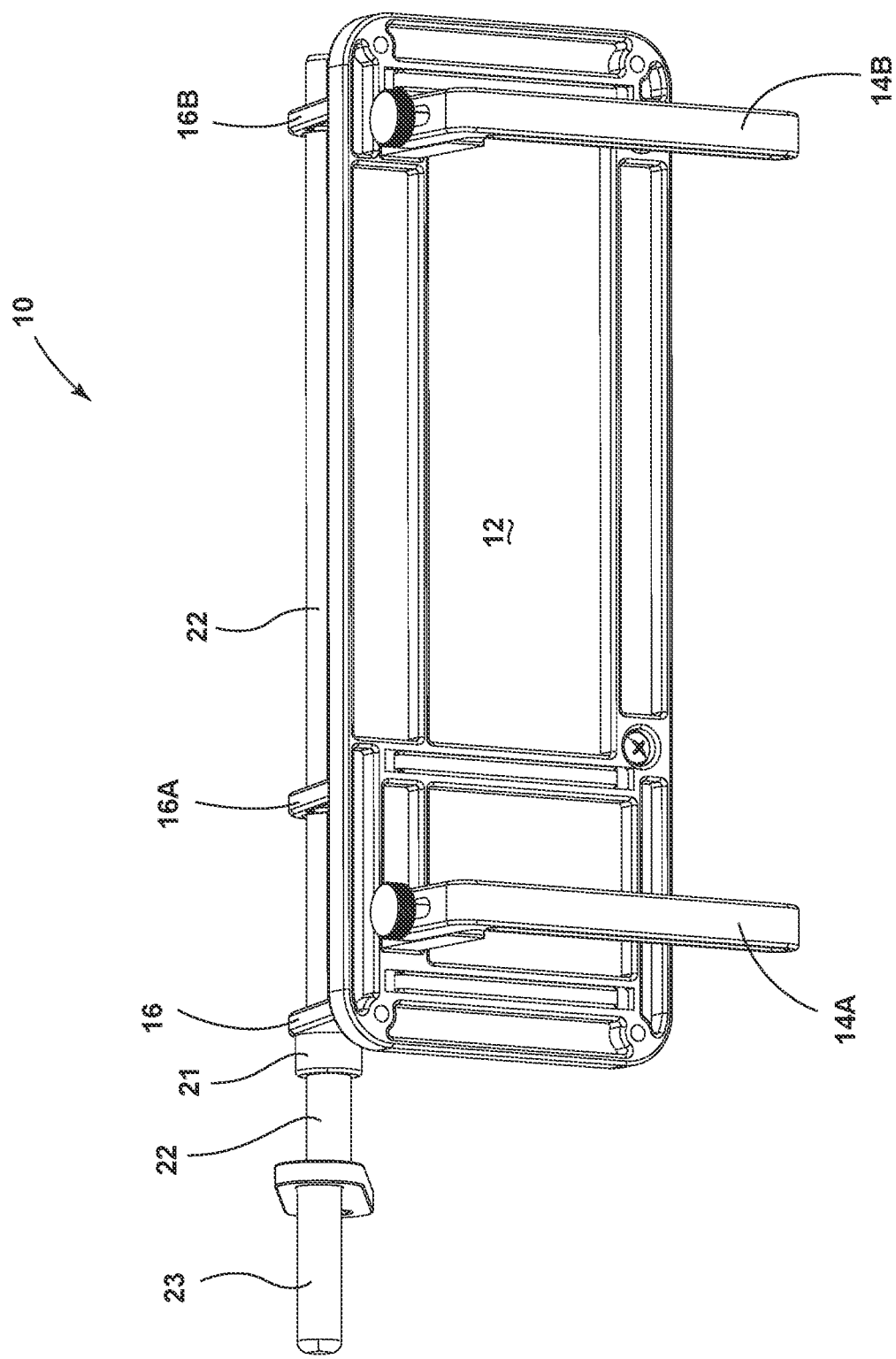
FIG. 15 is a rear-top-side perspective view of the embodiment of a wrapping or roll-up device shown in FIG. 10.
Figure 16:
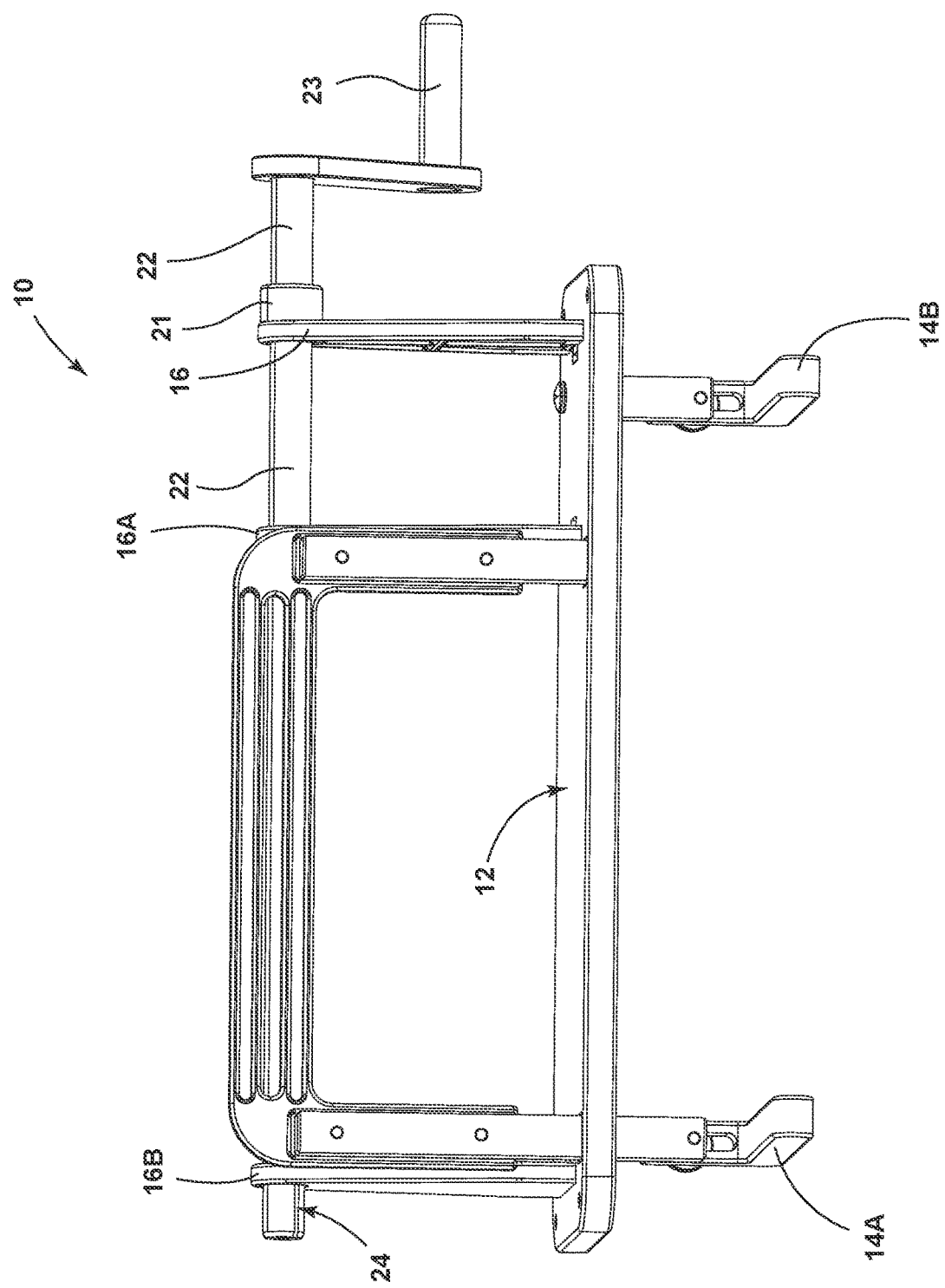
FIG. 16 is a bottom-front-side perspective view of the embodiment of a wrapping or roll-up device shown in FIG. 10.

In embodiments, such as generally illustrated, a handle 20 may include a stop 21 (or formation 25 as previously disclosed), an extended portion 22, a grip portion 23, and a slot 24. The one or more connectors may be as previously disclosed, and may be configured to provide portability to the device—e.g., permitting it to be readily moved from one location to another. Further, embodiments of a device 10 may include two connectors 14A, 14B that are spaced apart from one another at or about opposite ends of a base 1, and which may provide stability to the attachment of the device 10 to another object or apparatus (such as a portion of a stall wall). In embodiments, one of more connectors 14 may, for example, be provided to have an established, set, and/or standard width (e.g., a width of an open wall portion of a horse stall) or may instead be configured in a variety of manners to have an adjustable gap or width. In embodiments, for example as generally shown in FIGS. 10 and 14, the connectors 14A, 14B may include a slot 15 to permit adjustment of a gap/width and may further include a pin or screw 17 (e.g., a conventional screw, hand rotatable screw, or other fastener) to secure or fix a receiving gap/width between a portion of the connector 14A,14B and the base 12. For example and without limitation, in embodiments, a connector (e.g., 14, 14A, 14B) may be configured to hang through or over a portion of a grating or wall (such as a stall) having a width of between about 1.5 in. and about 2 in. and/or may hang-down on a back end between about 2 in. and about 4 in. Such dimensions may of course be modified to adapt to desired positioning and/or attachment to secure a device to various forms for support.

As generally shown in FIG. 10, at least one stop 21 may be included on a portion of the handle 20 and may be configured to prevent a slidable portion of the handle 20 from moving further into/past an aperture. For example, a stop 21 may comprise a formation with an expanded radius that prevents the handle from further sliding or moving through an aperture. With some embodiments a stop may comprise a unitarily formed portion of an extended portion of a handle. With other embodiments, a stop may comprise a separate/distinct component that is attached or connected to a portion of an extended portion of a handle. Additionally, as generally shown in the illustrated wrapping (or roll-up) device 10, embodiments of the device 10 may also optionally include a horizontally-spaced/remote receiving arm 16 and/or a formation 25, which may be associated with (e.g., configured to connect to or include) a cleaner/brush/scrapper or other feature associated with the device. For example, a formation 25, which may take a wide variety of sizes, shapes, materials, and forms and may include or present one or more cleaners, brushes, and/or scrapers to a wrap that is rolled up by the device. A remote receiving arm 16 may be provided at or about an opposing horizontal end of the device 10, and may include an aperture through the arm 16 or a receiving formation formed in the arm 16 to receive a remote portion of the handle 20 (which includes the slot therein), and/or may be configured to be fixed in position, such as shown (whether formed as a unitary part of the base 12 or whether connected thereto) or may be configured to move/rotate/pivot away from an extended portion of a handle 20. As with previously disclosed embodiments, arm 16 may be eliminated and, if desired, a separate guide or boundary-type formation may be employed to help guide an article to be wrapped.

FIGS. 11-16 generally illustrated different views of the embodiment of the wrapping device 10 shown in FIG. 10.

Figure 17:
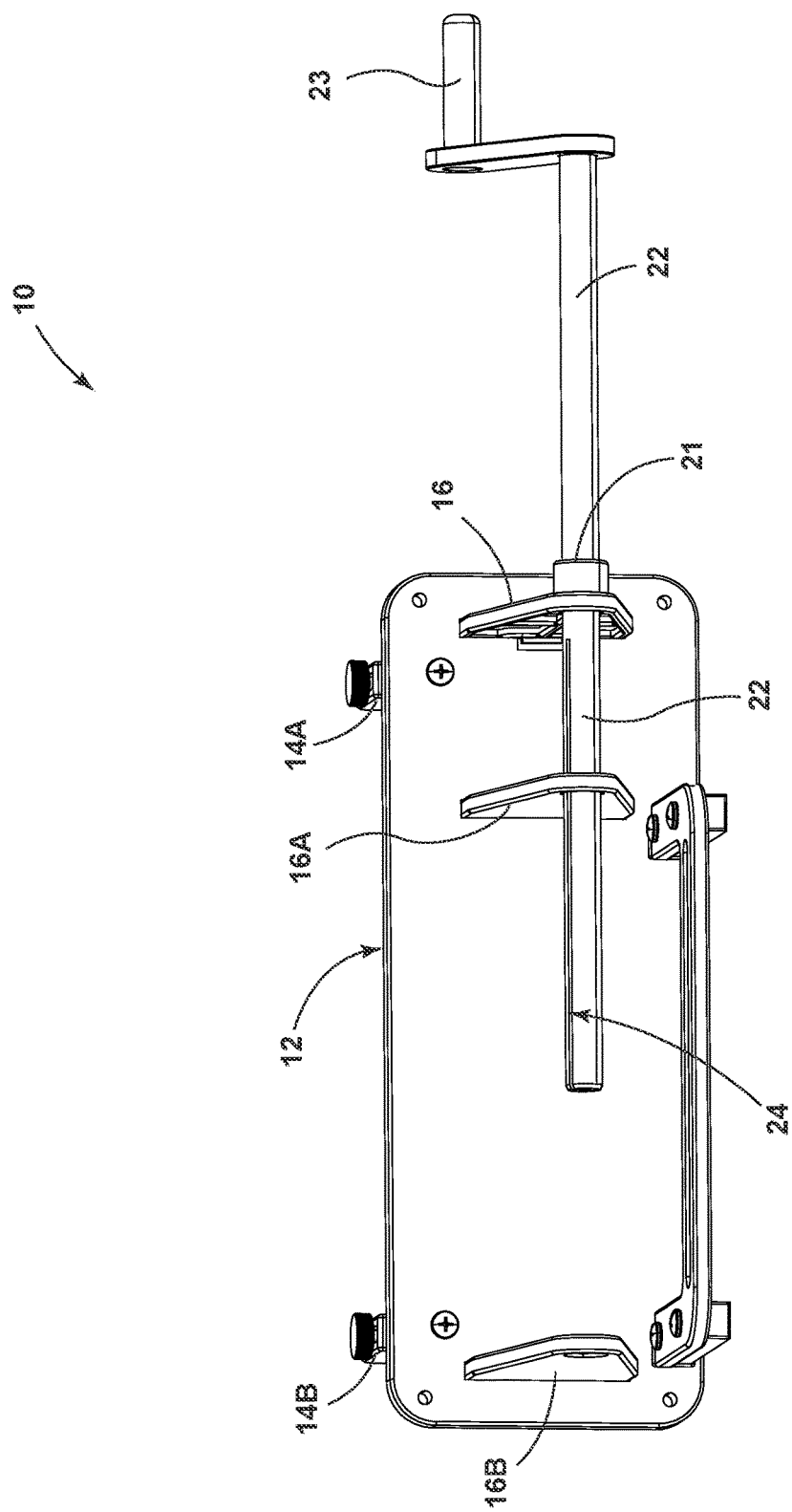
FIG. 17 is a front-top-side perspective view of the embodiment of a wrapping or roll-up device shown in FIG. 10, shown connected to a horizontal board.
Figure 18:
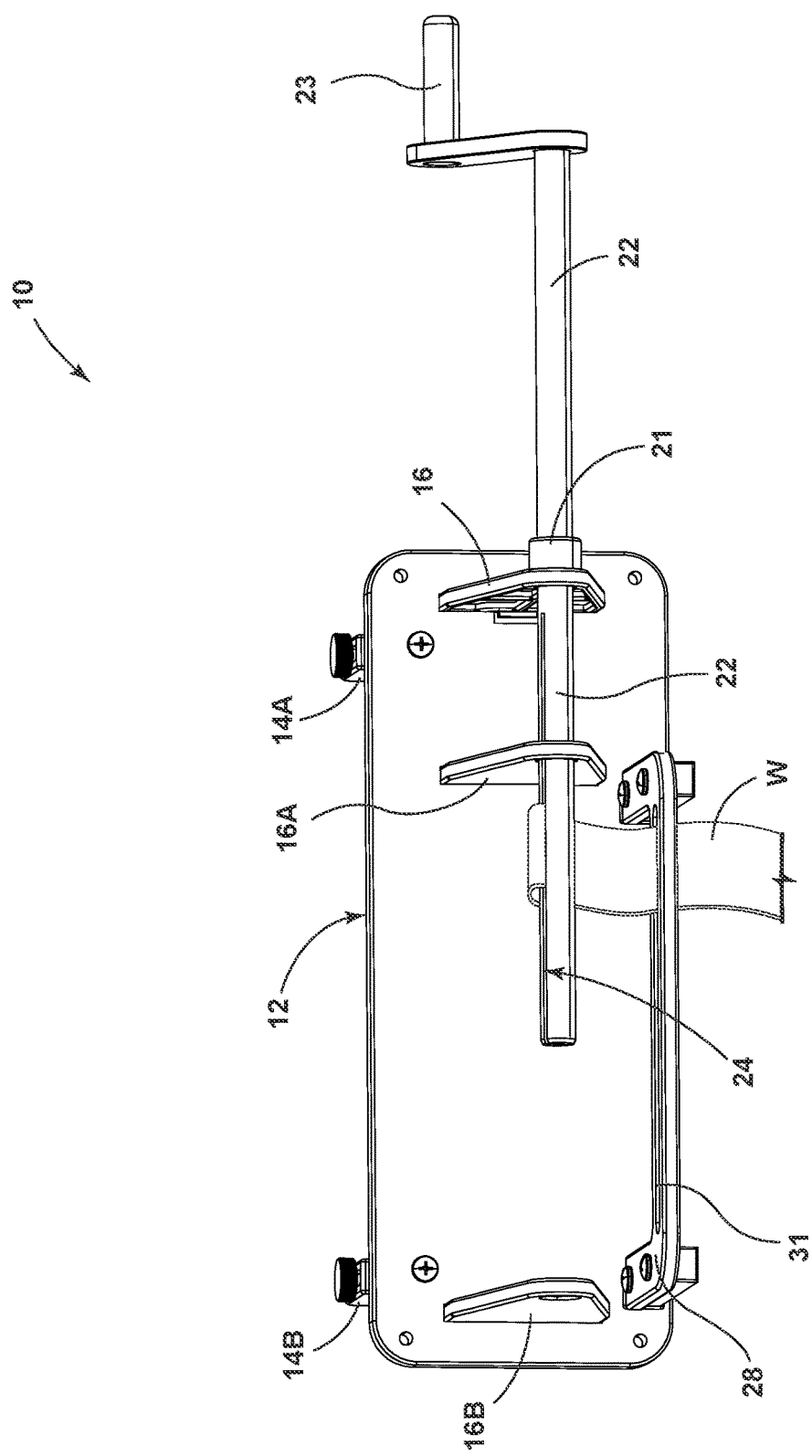
FIG. 18 is a front-top-side perspective view of the embodiment of a wrapping or roll-up device shown in FIG. 17 with a portion of a wrap inserted through the slot of the handle.
Figure 19:
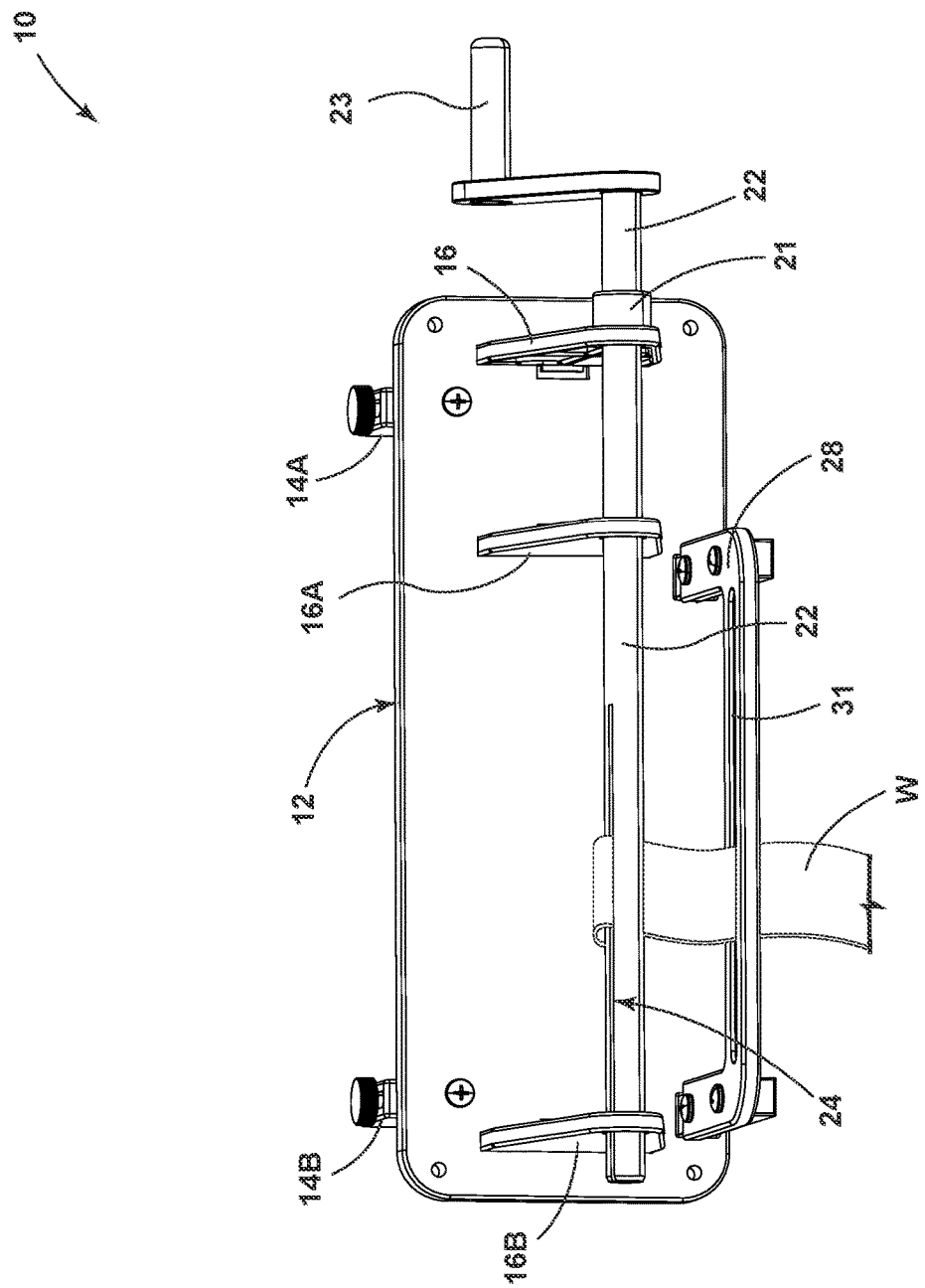
FIG. 19 is another front-top-side perspective view of the embodiment of a wrapping or roll-up device shown in FIG. 17 with a portion of a wrap inserted through the slot of the handle.
Figure 20:
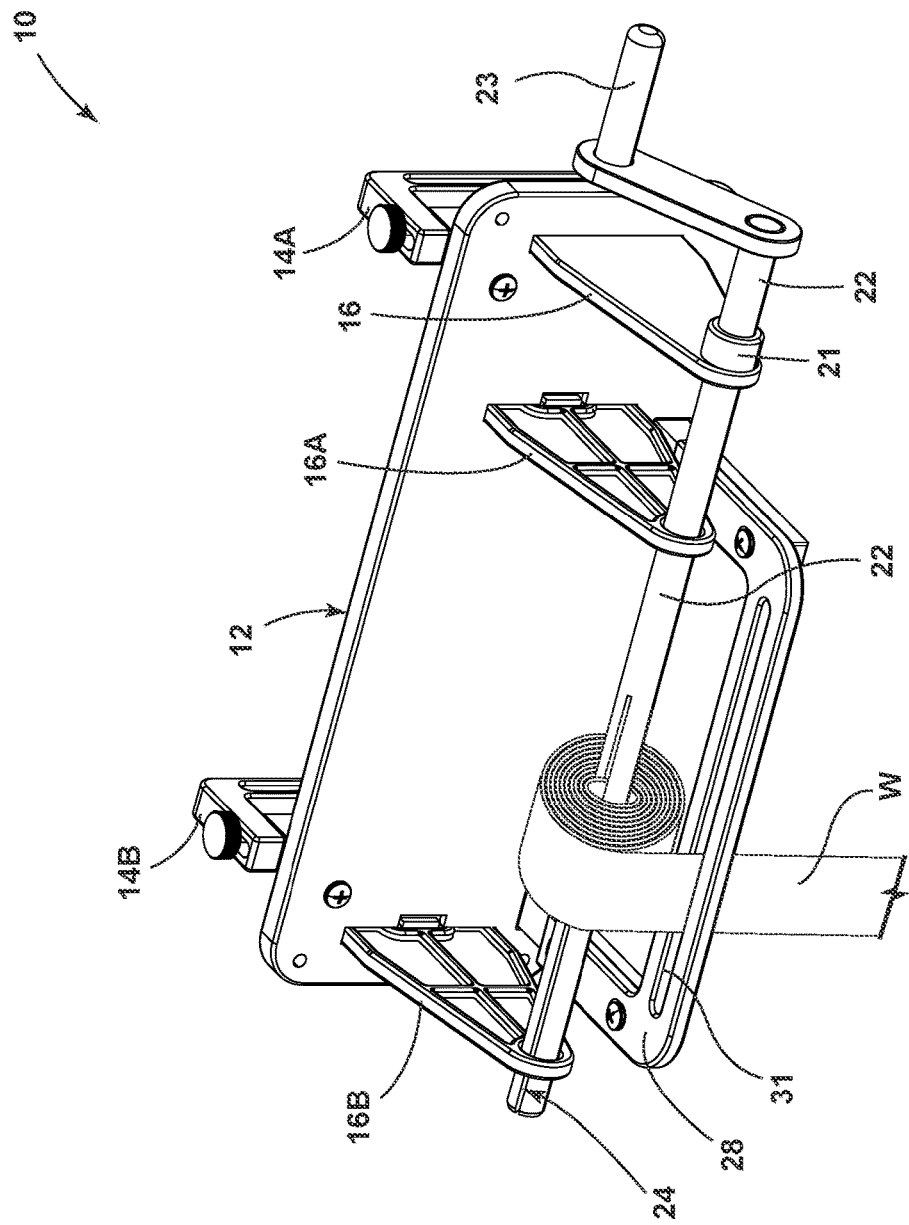
FIG. 20 is a front-top-side perspective view of the embodiment of a wrapping or roll-up device shown in FIG. 17 with a partially rolled wrap.
Figure 21:
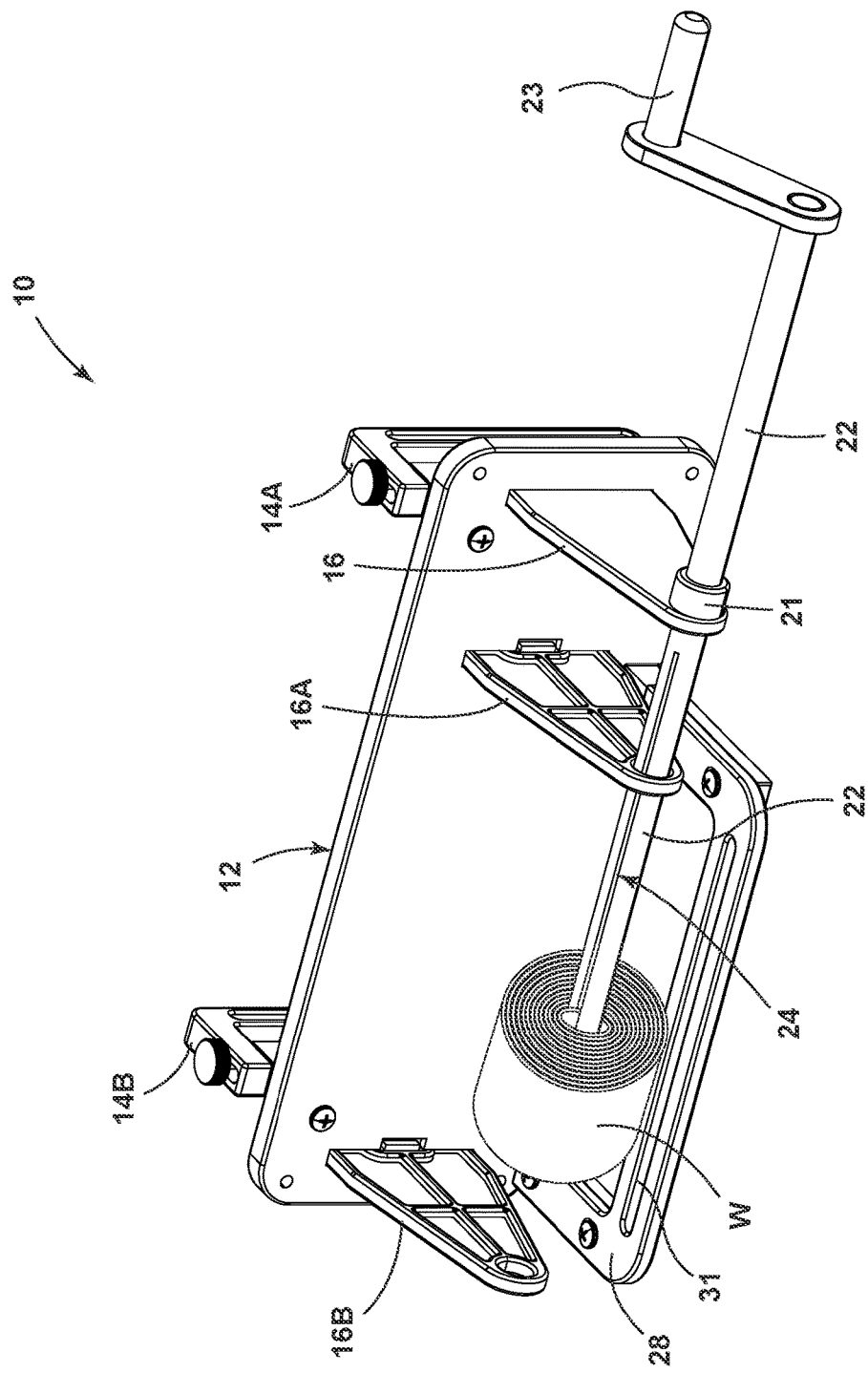
FIG. 21 is a front-top-side perspective view of the embodiment of a wrapping or roll-up device shown in FIG. 17 with substantially rolled up wrap.
Figure 22:
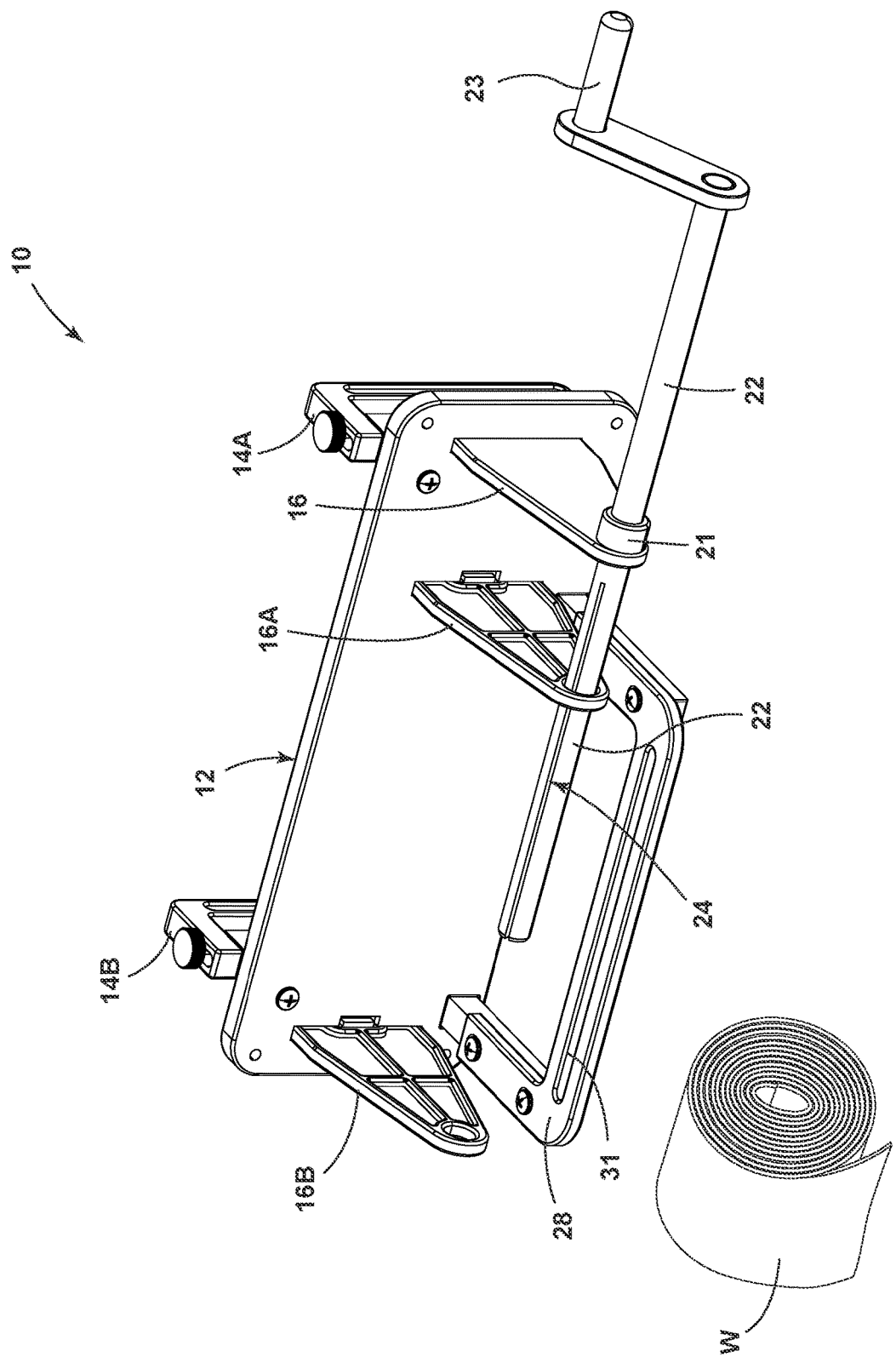
FIG. 22 is a front-top-side perspective view of the embodiment of a wrapping or roll-up device shown in FIG. 17 with a rolled wrap removed from the device.

FIGS. 17-22 generally illustrate an embodiment of a method of rolling a wrap in connection with an embodiment of a device such as previously disclosed. FIG. 17 generally shows a device 10 that may be attached to a wall or board (e.g., a portion of a stall wall) having a width. The one or more connectors 14 may connect/secure the device 10 to such wall or board. The device is shown with a handle 20 in a first (or a retracted) position relative to a receiving arm 16. Although, with embodiments that do not have a rigid receiving arm or formation, the handle 20 may not be required to be retracted as such. FIG. 18 generally illustrates how a portion or segment of an item to be wrapped (e.g., wrap W) may be positioned around a tensioner, or inserted through a slot 31 in a tensioner 28, and may further be inserted through a slot 24 in the extended portion 22 of the handle 20. FIG. 19 generally illustrates how a portion of the extended portion 22 of the handle 20 may be received by (or through) a receiving arm 16—for example, to provide added stability to the handle 20. FIG. 20 generally shows how, with the turning of the handle 20 (in a clockwise direction), the wrap W may be provided in a partially rolled-up condition. FIG. 21 generally illustrates the wrap W in a substantially fully rolled condition, FIG. 22 generally shows how the handle may be partially retracted and the wrap W may be removed from an end of the handle.

In embodiments, the wrapping device may be comprised of metal, or may be primarily or predominantly comprised of metal. Such metal may comprise aluminum, steel, or other metals known in the art. In other embodiments, the wrapping device may be comprised of plastic, or primarily or predominantly comprised of plastic. Such plastic may comprise various plastic and composite materials, including, for example and without limitation, reinforced plastics, such as fiber-reinforced polymers or plastics or glass-reinforced polymers or plastics. Composite materials may have a polymer matrix reinforced with fibers (such as glass, carbon, aramid, basalt, or others). It is noted that with an embodiment a handle (or portions thereof) and/or one or more connector(s) may be comprised of metal, while various other components of the wrapping device may be comprised of a plastic, polymer, and/or rubber (e.g., a scraper, if included). In some embodiments, the handle 20, the one or more connectors, and hardware (such as screws) may be comprised of metal and the base 12 and arms 16, 16A, 16B may be comprised of plastic.

Reference throughout the specification to "various embodiments," "with embodiments," "in embodiments," or "an embodiment," or the like, means that a particular feature, structure, or characteristic described in connection with the embodiment is included in at least one embodiment. Thus, appearances of the phrases "in various embodiments," "with embodiments," "in embodiments," or "an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment/example may be combined, in whole or in part, with the features, structures, functions, and/or characteristics of one or more other embodiments/examples without limitation given that such combination is not illogical or non-functional. Moreover, many modifications may be made to adapt a particular situation or material to the teachings of the present disclosure without departing from the scope thereof.

It should be understood that references to a single element are not necessarily so limited and may include one or more of such elements. Any directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of embodiments.

Joinder references (e.g., attached, coupled, connected, and the like) are to be construed broadly and may include intermediate members between a connection of elements and relative movement between elements. As such, joinder references do not necessarily imply that two elements are directly connected/coupled and in fixed relation to each other. The use of "e.g." and "for example" in the specification is to be construed broadly and is used to provide non-limiting examples of embodiments of the disclosure, and the disclosure is not limited to such examples. Uses of "and" and "or" are to be construed broadly (e.g., to be treated as "and/or"). For example, and without limitation, uses of "and" do not necessarily require all elements or features listed, and uses of "or" are inclusive unless such a construction would be illogical.

While processes, systems, and methods may be described herein in connection with one or more steps in a particular sequence, it should be understood that such methods may be practiced with the steps in a different order, with certain steps performed simultaneously, with additional steps, and/or with certain described steps omitted.

All matter contained in the above description or shown in the accompanying drawings shall be interpreted as illustrative only and not limiting. Changes in detail or structure may be made without departing from the present disclosure.

What is claimed is:

1. A wrapping or roll-up device, comprising:
   a base;
   one or more connectors connected to the base and configured to attach or connect the wrapping or roll-up device to a wall or support structure;
   a first arm extending from a portion of the base, the first arm including an aperture;
   a second arm extending from the base; and
   a handle including an extended portion and a grip portion, at least a portion of the extended portion configured to extend through the aperture;
   wherein the extended portion of the handle includes a slot disposed about an end of the extended portion remote from the grip portion, and the extended portion is configured to slide or translate back and forth through the aperture;
   wherein the second arm is pivotable or rotatable relative to the base and/or the extended portion.

2. The wrapping or roll-up device of claim 1, wherein the one or more connectors comprise one or more hooks.

3. The wrapping or roll-up device of claim 1, wherein the first arm extends substantially perpendicular to the base.

4. The wrapping or roll-up device of claim 1, wherein the one or more connectors comprise one or more screws, or fasteners.

5. The wrapping or roll-up device of claim 1, wherein a cleaner or brush is connected to the base, the arm, or the base and the arm.

6. The wrapping or roll-up device of claim 1, wherein the slot of the extended portion of the handle is configured to receive or retain a portion of an article to be rolled up.

7. The wrapping or roll-up device of claim 1, wherein the arm is integrally formed with the base as a unitary structure.

8. The wrapping or roll-up device of claim 1, wherein at least one of the one or more connectors is integrally formed with the base as a unitary structure.

9. The wrapping or roll-up device of claim 1, wherein the base and the arm are comprised of plastic.

10. The wrapping or roll-up device of claim 1, wherein the handle includes a stop or a radially extending formation configured as a bump or ridge.

11. The wrapping or roll-up device of claim 1, wherein the second arm includes a recess or an aperture configured to receive a portion of the extended portion.

12. The wrapping or roll-up device of claim 1, including a plate disposed on a side of the aperture of the arm.

13. The wrapping or roll-up device of claim 1, wherein one or more components are comprised of a metal.

14. A wrapping or roll-up device, comprising:
a base;
one or more connectors connected to the base and configured to attach or connect the wrapping or roll-up device to a wall or support structure;
an arm extending from a portion of the base, the arm including an aperture;
a handle including an extended portion and a grip portion, at least a portion of the extended portion configured to extend through the aperture; and
a holder configured to receive at least a portion of the extended portion of the handle, the holder includes a grip portion and a receiving portion;
wherein the extended portion of the handle includes a slot disposed about an end of the extended portion remote from the grip portion, and the extended portion is configured to slide or translate back and forth through the aperture; and the grip portion includes a portion configured to be grasped and/or held by a user and the receiving portion is configured to receive a portion of the extended portion of the handle.

15. A wrapping or roll-up device, comprising:
a base;
a first arm extending from a portion of the base and including an aperture;
a receiving arm extending from a portion of the base and including a receiving portion or an aperture, the receiving arm being laterally or horizontally offset from the first arm;
a second arm extending from a portion of the base and including an aperture, the second arm disposed laterally between the first arm and the receiving arm;
a handle including an extended portion and a grip portion, at least a portion of the extended portion configured to extend through the aperture of the first arm;
wherein the extended portion includes a slot disposed about an end of the extended portion remote from the grip portion, and the extended portion is configured to slide or translate back and forth through the aperture.

16. The wrapping or roll-up device of claim 15, including a tensioner.

17. The wrapping or roll-up device of claim 16, wherein the tensioner extends from the base and the tensioner includes a slot.

18. The wrapping or roll-up device of claim 15, including one or more connectors configured to connect the device to a wall or support.

19. The wrapping or roll-up device of claim 18, wherein the one or more connectors are configured to provide an adjustable gap or width between a portion of the one or more connectors and a portion of the base.

20. The wrapping or roll-up device of claim 19, wherein at least one connector comprises two components extending in a direction perpendicular to the base, one or both of the two components includes a slot, and a portion of a pin or screw extends through the slot and secures the two components together in position.

21. A method for wrapping or rolling up an article via the wrapping or roll-up device of claim 15, comprising:
securing the wrapping or roll-up device to a wall or support structure;
extending the handle with the slot through the aperture of the first arm of the device;
inserting a portion of the article through the slot of the handle;
extending the handle through the receiving arm;
rotating the handle to wrap or roll up the article about the handle;
pulling back the handle from the receiving arm and removing the article from the handle.

22. The wrapping or roll-up device of claim 15, wherein at least the base, the first arm, the second arm, and the receiving arm are comprised of plastic.

23. The wrapping or roll-up device of claim 15, wherein one or more of the first arm, the second arm, and the receiving arm are separate components connected to the base.

24. The wrapping or roll-up device of claim 15, wherein one or more of the first arm, the second arm, and the receiving arm are press-fit or snap connected to the base.

25. A wrapping or roll-up device, comprising:
a base comprised of plastic and extending in a vertical direction in a deployed state;
a separate first arm comprised of plastic and connected to the base, the first arm extending from a portion of the base and including an aperture comprising a through-hole;
a separate receiving arm comprised of plastic and connected to the base, the receiving arm extending from a portion of the base and including a receiving portion or an aperture, the receiving arm being laterally or horizontally offset along the base from the first arm;
a handle including an extended portion and a grip portion, at least a portion of the extended portion configured to extend through the through-hole of the first arm and up to or through the aperture of the receiving arm, the extended portion including a slot disposed about an end of the extended portion remote from the grip portion, and at least a segment of the extended portion configured to slide or translate back and forth through the through-hole;
a tensioner connected to and extending from the base, the tensioner including two portions separately connected to the base and a horizontally extending beam disposed vertically below the first arm and the receiving arm; and
at least one connector extending from the base on an opposite side of the first arm and the receiving arm, the connector including a portion that is perpendicular to the base and a portion that is offset from and parallel to the base.

* * * * *